| | | | | |
|---|---|---|---|---|
United States Patent [19] | | | [11] Patent Number: | 5,270,034 |
Cheng | | | [45] Date of Patent: | Dec. 14, 1993 |

[54] TRANSLUCENT ANTIPERSPIRANT STICK COMPOSITION

[76] Inventor: Guang-Yu Cheng, c/o F&C International, Inc. 599 Johnson Ave., Brooklyn, N.Y. 11237

[21] Appl. No.: 868,005

[22] Filed: Apr. 14, 1992

[51] Int. Cl.$^5$ ............................ A61K 7/32; A61K 7/38
[52] U.S. Cl. ................................ 424/68; 424/DIG. 5; 424/65
[58] Field of Search ............................ 424/68, DIG. 5

[56] References Cited

U.S. PATENT DOCUMENTS

| | | | |
|---|---|---|---|
| 3,255,082 | 6/1966 | Barton | 424/68 |
| 3,887,692 | 6/1975 | Gilman | 424/68 |
| 3,904,741 | 9/1975 | Jones et al. | 424/68 |
| 4,137,306 | 1/1979 | Rubino et al. | 424/68 |
| 4,154,816 | 5/1979 | Roehl et al. | 424/68 |
| 4,279,658 | 7/1981 | Harvey et al. | 424/68 |
| 4,302,443 | 11/1981 | de Nauarre et al. | 424/68 |
| 4,346,079 | 8/1982 | Roehl | 424/68 |
| 4,359,456 | 11/1982 | Gosling et al. | |
| 4,518,582 | 5/1985 | Schamper et al. | 424/68 |
| 4,722,835 | 2/1988 | Schamper et al. | 424/68 |
| 4,743,444 | 5/1988 | McCall | 424/68 |
| 4,816,261 | 3/1989 | Luebbe et al. | 424/68 |
| 4,822,602 | 4/1989 | Sabatelli | 424/68 |
| 4,944,937 | 7/1990 | McCall | 424/68 |
| 4,944,938 | 7/1990 | Potini | 424/68 |
| 4,948,578 | 8/1990 | Burger et al. | 424/DIG. 5 |

FOREIGN PATENT DOCUMENTS 0451002 10/1991 European Pat. Off. ............ 424/68

Primary Examiner—Dale R. Ore

[57] ABSTRACT

An antiperspirant stick composition is provided. The antiperspirant composition comprises: (a) from about 15% to about 25% by weight of an acidic antiperspirant active metal salt; (b) from about 1% to about 70% by weight of a polar solvent which is not a monohydric alcohol; (c) from about 5% to about 15% by weight of an aprotic solvent; (d) from about 2% to about 5% by weight of a gelling agent; and (e) from about 0.05% to about 0.3% by weight of an antimicrobial agent. The antiperspirant composition is stable without the inclusion of a stabilizing agent and also is relatively odorless and clear resulting in an aesthetically desirable antiperspirant composition which eliminates the need for masking fragrances.

20 Claims, No Drawings

TRANSLUCENT ANTIPERSPIRANT STICK COMPOSITION

BACKGROUND OF THE INVENTION

The present invention relates to an antiperspirant composition, and more particularly, to an alcohol-based antiperspirant stick composition containing an acidic antiperspirant active compound in the presence of a gelling agent wherein the composition is stable at room temperature as well as at elevated temperatures.

The art is replete with formulations of stick-type cosmetics for various uses, such as antiperspirants and deodorants. The specific stick-type formulation varies depending upon such factors as the intended use, the "active" ingredient to be incorporated, and the part of the body to which the stick-type formulation is to be applied. As is well known in the art of antiperspirants, there are three main types of antiperspirant stick formulations, namely, compressed powdered sticks, gel sticks and wax sticks While each of these types of formulations has advantages depending upon the particular application, each formulation also possesses several disadvantages. For example, compressed powdered sticks are often brittle and hard and leave an aesthetically unacceptable dust upon application. Similarly, wax sticks also yield aesthetically unacceptable products due to factors such as hardness, greasiness and stickiness.

In the past, antiperspirant sticks of the gel type have been typically based on alcoholic or hydroalcoholic systems which have been gelled with sodium stearate (soap). However, ordinary aluminum salts are incompatible with a soap-alcohol system, resulting in the formation of insoluble soaps which prevent solidification or gelling of the stick. This result is undesirable and defeats the purpose for which such an antiperspirant stick is directed. Although a sodium aluminum chlorohydroxy lactate complex has been found to be compatible with typical soap-based sticks, such a complex merely functions as a deodorant as it provides only from about 10-12% sweat reduction. Since gel-type sticks have advantages over both compressed powder and wax sticks in that they leave very little residue or dust and provide a vehicle which glides easily over the skin surface, it would be desirable to have an alcohol-based antiperspirant stick composition which provides improved sweat reduction while maintaining a stable gel.

Several attempts have been made to overcome these disadvantages. For example, Roehl et al, U.S. Pat. No. 4,346,079 and Roehl et al, U.S. Pat. No. 4,154,816 include the use of dibenzaldehyde monosorbitol acetal (DBMSA) as a gelling agent to produce a more stable solid antiperspirant gel. Nevertheless, it has been found that such antiperspirant compositions, while avoiding the use of soaps, may produce antiperspirant compositions having aesthetically unacceptable stickiness. Further, such antiperspirants are not stable upon extended exposure to temperatures exceeding room temperature. As a result, there is a need for an antiperspirant composition that is not only stable at elevated temperatures, but also possesses aesthetically acceptable features such as hardness and clarity or translucentness.

In the past, antiperspirant compositions of the gel type have been unstable at elevated temperatures and even at room temperature. To that end, Schamper et al, U.S. Pat. No. 4,518,582, provide an antiperspirant composition containing a dibenzyl monosorbitol acetal gelling agent in the presence of an antiperspirant active metal salt which is taught to be stable at elevated temperatures. Schamper et al, however, require the addition of a gel stabilizer to prevent or retard deterioration of the gelled compositions at such temperatures. The inclusion of such gel stabilizers causes the antiperspirant to be hazy or cloudy which is aesthetically unacceptable. Furthermore, past antiperspirant compositions typically use excessive amounts of monohydric alcohols, such as ethanol, which tend to deteriorate and desolidify or liquidate the antiperspirant composition, especially at elevated temperatures. Additionally, the monohydric alcohol potentially can react with the dibenzyl monosorbitol acetal to form a different acetal, thereby decreasing the antiperspirant properties of the composition. It would therefore be desirable to have an antiperspirant composition which is stable at room temperature as well as elevated temperatures without the use of a gel stabilizer.

Other antiperspirant sticks currently in wide use are based on volatile silicone oil, stearyl or cetyl alcohol and aluminum chlorohydrate. Such antiperspirant compositions are relatively efficient, easy to apply, and have non-sting properties. However, these antiperspirant compositions also suffer from several drawbacks. For example, those antiperspirant compositions do not provide uniform settling of the components of the composition, which is caused by the lack of solubility of the inorganic salt component in the molten wax or gel phase. Uniform settling or distribution of all the components in the antiperspirant composition is extremely important since it is required by the Food & Drug Administration (FDA) for Over-The-Counter (OTC) drugs. Another disadvantage of these antiperspirant compositions relates to aesthetics in that they leave a white residue which is undesirable. Finally, as stated above, past antiperspirant compositions typically use large amounts of monohydric alcohols, such as ethanol, which lead to instability and produce unacceptable odors necessitating the incorporation of excess quantities of fragrances to mask such undesirable odors.

Accordingly, the need exists in the art for an alcohol-based antiperspirant stick composition of the gel type which does not contain gel stabilizers and excessive amounts of monohydric alcohols yet remains stable at room temperature as well as at elevated temperatures. There is also a need in the art for an antiperspirant composition in which the individual constituents are uniformly distributed upon gel formation. Finally, there is a need for a more inexpensive antiperspirant composition which has improved sweat reduction properties while providing aesthetically desirable features such as a high degree of clarity or translucentness as well as being substantially odorless.

SUMMARY OF THE INVENTION

The present invention meets the aforementioned needs in the art by providing an alcohol-based antiperspirant stick composition of the gel type. The antiperspirant composition does not contain gel stabilizers yet remains stable at room temperature as well as at higher temperatures resulting in a substantial improvement over those antiperspirant compositions used in the past. In addition, the individual constituents in the present antiperspirant composition are uniformly distributed upon gel formation, thereby leading to an antiperspirant composition having excellent efficacy and clarity or translucentness. Finally, the invention provides an antiperspirant composition which has improved sweat reduction without the incorporation of monohydric alcohols yet maintains aesthetically desirable features such as a substantially odorless and translucent gel. As used herein, the term antiperspirant refers to a composition having the capability of sweat reduction as well as the ability to deodorize for cosmetic purposes.

In accordance with one aspect of the invention, an antiperspirant stick composition is provided. The antiperspirant composition comprises (a) from about 15% to about 25% by weight of an acidic antiperspirant active metal salt; (b) from about 1% to about 70% by weight of a polar solvent which is not a monohydric alcohol; (c) from about 5% to about 15% by weight of an aprotic solvent; (d) from about 2% to about 5% by weight of a gelling agent; and (e) from about 0.05% to about 0 3% by weight of an antimicrobial agent. The acidic antiperspirant active metal salt may comprise a complex of aluminum chlorohydrate and propylene glycol. Preferably, the polar solvent is selected from the group consisting of propylene glycol, hexylene glycol, dipropylene glycol, dimethicone copolyol, dipropyl glycol methyl ether, ethylene glycol phenyl ether, isostearyl alcohol and benzyl alcohol.

The term aprotic solvent, as used herein, refers to polar solvents with a moderately high dielectric constant which does not contain acidic hydrogen such that it cannot offer or accept protons. The aprotic solvent is preferably selected from the group consisting of lactamide monoethanolamine and N-methylpyrrolidone. The use of the aprotic solvent provides a substantial improvement in that it eliminates the need for excessive amounts, typically more than 40% by weight, of monohydric alcohols used in past antiperspirant compositions. This is desirable since such monohydric alcohols are more reactive with respect to gelling agents such as dibenzyl monosorbitol acetal which leads to instability of the antiperspirant composition, especially at elevated temperatures. Such monohydric alcohols also emit strong odors thereby necessitating the incorporation of fragrances, a problem not experienced with the present composition which contains aprotic solvents. Additionally, the preferred gelling agent for the antiperspirant composition is dibenzyl monosorbitol acetal The preferred antimicrobial agent comprises 2,4,4'-trichloro-2'-hydroxydiphenyl ether.

In accordance with another aspect of the invention, a method of making an antiperspirant stick composition as described above is provided. The method comprises the steps of preparing a first mixture by dissolving an acidic antiperspirant active metal salt in a first polar solvent, and preparing a second mixture by dissolving a gelling agent in a second polar solvent and an aprotic solvent. Thereafter, the first mixture is poured into the second mixture so as to obtain a clear or translucent homogenous solution. The homogenous solution is then poured into a mold having a predetermined shape and allowed to gel, thereby forming the present antiperspirant stick composition. Preferably, the first mixture is prepared by simultaneously mixing and heating the active metal salt and the first polar solvent so as to dissolve the active metal salt in the first polar solvent. Similarly, the second mixture is preferably prepared by simultaneously mixing and heating the gelling agent in the second polar solvent and the aprotic solvent so as to dissolve the gelling agent in the second polar solvent and the aprotic solvent.

Accordingly, it is an object of the present invention to provide an alcohol-based antiperspirant stick composition of the gel type which does not contain gel stabilizers yet remains stable at room temperature as well as at higher temperatures; it is also an object of the invention to provide such an antiperspirant composition in which the individual constituents are uniformly distributed upon gel formation; and, it is an object of the invention to provide a more inexpensive antiperspirant composition which has improved sweat reduction while maintaining aesthetically desirable features such as being substantially odorless and clear or translucent. Other objects and advantages of the invention will be apparent from the following detailed description and the appended claims.

DETAILED DESCRIPTION OF THE INVENTION

The alcohol-based antiperspirant stick composition of the invention is of the gel type and does not contain gel stabilizers yet remains stable at room temperature as well as at higher temperatures. As stated above, the preferred antiperspirant composition comprises: (a) from about 15% to about 25% by weight of an acidic antiperspirant active metal salt; (b) from about 1% to about 70% by weight of a polar solvent which is not a monohydric alcohol; (c) from about 5% to about 15% by weight of an aprotic solvent; (d) from about 2% to about 5% by weight of a gelling agent; and (e) from about 0.05% to about 0.3% by weight of an antimicrobial agent. The individual constituents in the antiperspirant composition are uniformly distributed upon gel formation, thereby leading to an antiperspirant composition having excellent efficacy. Also, the antiperspirant composition is less expensive and has improved sweat reduction while providing aesthetically desirable features such as being substantially odorless and clear or translucent.

While the above-mentioned constituents are necessary in providing an antiperspirant composition having the desired features described herein, it should be understood that additional constituents may be incorporated therein without departing from the scope of the invention. All of the constituents, however, must be "cosmetically acceptable" in that they must be safe for human use as mandated by the current Food & Drug Administration (FDA) regulations as well as aesthetically acceptable. To that end, the acidic antiperspirant active metal salt preferably comprises a complex of aluminum chlorohydrate and propylene glycol which is available from a variety of sources. The most preferred complex, however, is purchased under the trademark Rehydroll II from Reheis Corp., N.J., and has the following formula:

$$[Al_2(OH)_5]_n \cdot nCl$$

wherein n is from 1 to about 6. It should be understood that n may be of a non-integer value.

Alternative aluminum salts can be substituted for the preferred complex, as described above, without departing from the scope of the invention. For example, aluminum salts produced in accordance with the teachings of the following references, all of which are incorporated herein by reference, may be used: Gilman, U.S. Pat. No. 3,887,692; Jones et al, U.S. Pat. No. 3,904,741; and, Gosling et al, U.S. Pat. No. 4,359,456. Although not preferable her astringent metallic salts, such as zirconium and zinc salts, may be used in the antiperspirant composition of the invention.

As those skilled in the art will understand, the selection of the polar solvent and the aprotic solvent will vary depending on the characteristics of the antiperspirant composition desired. In particular, the polar solvent as well as the aprotic solvent are useful in the antiperspirant composition for purposes of providing cosmetic benefits such as emolliency and a cooling sensation upon application to the user's skin. The preferable polar solvent is not a monohydric alcohol which eliminates the offensive odor emitted by past antiperspirant compositions. It is preferable for the polar solvent to be selected from the group consisting of polyhydric alcohols and branched chain alcohols. To that end, the polar solvent is most preferably selected from the group consisting of propylene glycol, hexylene glycol, dipropylene glycol, dimethicone copolyol, dipropyl glycol methyl ether, ethylene glycol phenyl ether, isostearyl alcohol and benzyl alcohol. As those skilled in the art will appreciate, the polarity of such solvents is relatively weak.

As stated previously, aprotic solvents, as defined herein, refer to those solvents with moderately high dielectric constants which do not contain acidic hydrogen such that it cannot offer or accept protons. It should be understood that while only a few of the aprotic solvents are disclosed herein, all aprotic solvents as defined herein can be used in the antiperspirant composition of the present invention. Preferably, however, the aprotic solvent is selected from the group consisting of lactamide monoethanolamine and N-methylpyrrolidone. Other aprotic solvents which, although not preferred, can be used include hexamethylphosphoroastriamide (HMPA), crown ether, dimethylfuran (DMF), and dimethylacetalamide. The use of the aprotic solvent provides a substantial improvement over past antiperspirant compositions in that it eliminates the need for excessive amounts of protic solvents, such as monohydric alcohols, used in past antiperspirant compositions which emitted strong offensive odors. The strong odors emitted by protic alcohols necessitated the incorporation of fragrances so as to mask the annoyance of such odors.

As discussed previously, this problem is not experienced with the present antiperspirant composition since the aforementioned aprotic solvent reduces the need for protic solvents in the composition. The most preferred aprotic solvent is lactamide monoethanolamine sold under the trademark Incromectant LMEA from Croda Inc., having the formula:

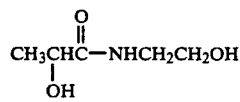

The aprotic solvent N-methylpyrrolidone is well known in the art and commercially available from a variety of sources including but not limited to International Specialty Products, N.J., sold under the product name N-Pyrol and having the formula:

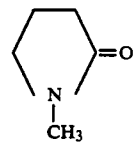

Both of these aprotic solvents are especially capable of solvating cations and possess a relatively high dielectric constant so as to render them excellent solvents for many covalent compounds and for numerous salts, as well. Additionally, because of their capability of dissolving a wide spectrum of polymers combined with their high degree of stability, such aprotic solvents are widely used as a gelling agent solvent. Moreover, the protic solvents previously used caused past antiperspirant compositions to be relatively unstable as well as less clear or translucent as compared to the present antiperspirant composition containing aprotic solvents which provide a composition which has greater clarity with increased stability.

The antiperspirant composition preferably includes a benzylidene sorbitol to serve as the gelling agent. As mentioned previously, the most preferred benzylidene sorbitol for use in the present antiperspirant composition is dibenzyl monosorbitol acetal (DBMSA). This material is well known and generally disclosed in Schamper et al, U.S. Pat. No. 4,518,582, the disclosure of which is incorporated herein by reference. Furthermore, dibenzyl monosorbitol acetal is commercially available from, for example, New Japan Chemical Co., Ltd. under the trademark Gell-All-D and Milliken Chemical, Division of Milliken & Company, and under the product name Millithix 925.

The present antiperspirant composition also comprises an antimicrobial agent generally to serve as a deodorant. The preferred antimicrobial agent comprises 2,4,4'-trichloro-2'-hydroxydiphenyl ether which is well known and commercially available. For example, 2,4,4'-trichloro-2'-hydroxydiphenyl ether can be purchased from Ciba Geigy Corporation under the product name Irgasan DP-300. It should be understood by those skilled in the art that safe and effective amounts of other deodorant materials may be incorporated into the present antiperspirant composition. To that end, bactericides and fungicides and mixtures thereof can be used. In that regard, suitable deodorants include bacteriostatic quaternary ammonium bromide, cetyl pyridinium chloride, benzethonium chloride, diisobutyl phenoxy thoxy ethyl dimethyl benzyl ammonium chloride, sodium N-lauryl-sarcosine, sodium N-polymethyl sarcosine, lauryl sarcosine, N-myristyl glycine, potassium N-lauryl sarcosine, stearyl trimethyl ammonium chloride, sodium bicarbonate, diaminoalkyl amide, and mixtures thereof.

As will be appreciated by those skilled in the art, the present antiperspirant composition can also include several optional components which are commonly used in the art for purposes of modifying the physical characteristics of the antiperspirant composition. For example, hardeners, strengtheners, colorants, and perfumes may be incorporated into the antiperspirant composition without departing from the scope of the invention. Such optional components are disclosed in Barton, U.S. Pat. No. 3,255,082, Rubino et al, U.S. Pat. No. 4,137,306 and Hooper et al, U.S. Pat. No. 4,279,658, all of which are incorporated herein by reference.

In accordance with the present invention, a more preferred antiperspirant composition comprises: (a) from about 15% to about 25% by weight of a complex of aluminum chlorohydrate and propylene glycol; (b) from about 1% to about 70% by weight of a polar solvent selected from the group consisting of propylene glycol, hexylene glycol, dipropylene glycol, dimethicone copolyol, dipropyl glycol methyl ether, ethylene glycol phenyl ether, isostearyl alcohol and benzyl alcohol; (c) from about 5% to about 15% by weight of an aprotic solvent selected from the group consisting of lactamide monoethanolamine and N-methylpyrrolidone; (d) from about 2% to about 5% by weight of a gelling agent; and (e) from about 0.05% to about 0.3% by weight of an antimicrobial agent.

Further, another preferred antiperspirant composition comprises: (a) about 15% by weight complex of aluminum chlorohydrate and propylene glycol; (b) about 35% by weight propylene glycol; (c) from about 10% to about 20% by weight dipropylene glycol; (d) from about 10% to about 20% by weight dipropylene glycol methyl ether; (e) about 10% by weight of an aprotic solvent; (f) from about 5% to about 25% by weight of a branched chain alcohol; (g) about 3% by weight dibenzyl monosorbitol acetal; and (h) about 0.3% by weight 2,4,4'-trichloro-2'-hydroxydiphenyl ether.

In yet another preferred antiperspirant composition, the antiperspirant composition comprises: (a) about 15% by weight complex of aluminum chlorohydrate and propylene glycol; (b) about 35% by weight propylene glycol; (c) from about 10% to about 20% by weight of hexylene glycol; (d) from about 10% to about 20% by weight of ethylene glycol phenyl ether; (e) about 10% by weight of an aprotic solvent selected from the group consisting of lactamide monoethanolamine and N-methylpyrrolidone; (f) from about 5% to about 25% by weight of a branched chain alcohol; (g) about 3% by weight dibenzyl monosorbitol acetal; and (h) about 0.3% by weight 2,4,4'-trichloro-2'-hydroxydiphenyl ether. The preferred branched chain alcohols for each of the aforedescribed preferred antiperspirant compositions are selected from the group consisting of isostearyl alcohol and benzyl alcohol. It should be understood that all of the individual constituents described above with respect to the preferred compositions are the same as described in detail previously.

In accordance with another aspect of the invention, a method of making the antiperspirant composition as described above is provided. The method comprises the steps of preparing a first mixture by dissolving the acidic antiperspirant active metal salt in one of the polar solvents described above, and preparing a second mixture by dissolving the gelling agent in a solution of another polar solvent and the aprotic solvent. Thereafter, the first mixture is poured into the second mixture so as to obtain a clear or translucent homogenous solution. The homogenous solution is then poured into a mold having a predetermined shape, typically the shape of a stick, although it should be understood that the mold may have any shape which finds commercial success. The homogenous solution is then allowed to gel or cure, thereby forming the present antiperspirant composition.

Preferably, the first mixture is prepared by simultaneously mixing and heating the active metal salt and the polar solvent so as to dissolve the active metal salt completely in the polar solvent. The temperature will vary depending upon the relative proportions but should be sufficiently high so as to completely dissolve the active metal salt. Typically this temperature will be around 80° C. Similarly, the second mixture is preferably prepared by simultaneously mixing and heating the gelling agent in the polar solvent and the aprotic solvent so as to dissolve the gelling agent completely, as well. The typical temperature will be around 90° C. Although the polar solvent in the first mixture and the polar solvent in the second mixture have been described herein as being different, it should be understood that the same polar solvent may be used in both the first mixture and the second mixture without departing from the scope of the invention.

Those skilled in the art should appreciate that the other constituents described herein are dissolved into either the first mixture or the second mixture depending upon the particular constituent. For example, the antimicrobial agent is preferably dissolved into the first mixture so as to provide the antiperspirant composition with the desired deodorant features. Similarly, the other possible constituents can be dissolved appropriately.

The following examples are presented for purposes of illustrating the present invention only and are not to be considered as limiting the scope of invention.

EXAMPLE I

An antiperspirant stick composition was produced by combining two separate mixtures and then combining the mixture to form a gel as described above. The individual constituents of the two mixtures are listed below.

| Constituent | % (by weight) |
| --- | --- |
| First Mixture: | |
| Propylene Glycol | 34.7 |
| Rehydrol II[1] | 15.0 |
| Benzyl Alcohol | 17.0 |
| Dow Corning 193[2] | 5.0 |
| Irgasan DP-300[3] | 0.3 |
| Second Mixture: | |
| Hexylene Glycol | 20.0 |
| Lactamide MEA[4] | 5.0 |
| DBMSA[5] | 3.0 |

[1] A complex of aluminum chlorohydrate and propylene glycol purchased under the trademark Rehydrol II from Reheis Corp., New Jersey.
[2] A dimelthicone copolyol from Dow Corning, Midland, Michigan.
[3] A 2,4,4'-trichloro-2'-hydroxydiphenyl ether can be purchased from Ciba Geigy Corporation under the product name Irgasan DP-300.
[4] An aprotic solvent, lactamide monoethanolamine, sold under the trademark Incromectant LMEA from Croda Inc.
[5] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE II

The following antiperspirant composition was made as described in Example I. The first mixture and the second mixture contained the following constituents.

| Constituent | % (by weight) |
| --- | --- |
| First Mixture: | |
| Propylene Glycol | 34.7 |
| Rehydrol II[1] | 15.0 |
| Dipropylene Glycol Methyl Ether | 22.0 |
| Isostearyl Alcohol | 5.0 |
| Irgasan DP-300[2] | 0.3 |

| Constituent | % (by weight) |
|---|---|
| Second Mixture: | |
| Dipropylene Glycol | 10.0 |
| Lactamide MEA[3] | 5.0 |
| N-methylpyrrolidone | 5.0 |
| DBMSA[4] | 3.0 |

[1] A complex of aluminum chlorohydrate and propylene glycol purchased under the trademark Rehydrol II from Reheis Corp., New Jersey.
[2] A 2,4,4'-trichloro-2'-hydroxydiphenyl ether can be purchased from Ciba Geigy Corporation under the product name Irgasan DP-300.
[3] An aprotic solvent, lactamide monoethanolamine, sold under the trademark Incromectant LMEA from Croda Inc.
[4] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE III

The following antiperspirant composition was made as described in Example I. The first mixture and the second mixture contained the following constituents.

| Constituent | % (by weight) |
|---|---|
| First Mixture: | |
| Propylene Glycol | 34.7 |
| Rehydrol II[1] | 15.0 |
| Benzyl Alcohol | 17.0 |
| Irgasan DP-300[2] | 0.3 |
| Second Mixture: | |
| Dipropylene Glycol | 20.0 |
| Lactamide MEA[3] | 5.0 |
| N-methylpyrrolidone | 5.0 |
| DBMSA[4] | 3.0 |

[1] A complex of aluminum chlorohydrate and propylene glycol purchased under the trademark Rehydrol II from Reheis Corp., New Jersey.
[2] A 2,4,4'-trichloro-2'-hydroxydiphenyl ether can be purchased from Ciba Geigy Corporation under the product name Irgasan DP-300.
[3] An aprotic solvent, lactamide monoethanolamine, sold under the trademark Incromectant LMEA from Croda Inc.
[4] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE IV

The following antiperspirant composition was made as described in Example I. The first mixture and the second mixture contained the following constituents.

| Constituent | % (by weight) |
|---|---|
| First Mixture: | |
| Propylene Glycol | 34.7 |
| Rehydrol II[1] | 15.0 |
| Dipropylene Glycol Methyl Ether | 22.0 |
| Isostearyl Alcohol | 5.0 |
| Irgasan DP-300[2] | 0.3 |
| Second Mixture: | |
| Hexylene Glycol | 15.0 |
| Lactamide MEA[3] | 5.0 |
| DBMSA[4] | 3.0 |

[1] A complex of aluminum chlorohydrate and propylene glycol purchased under the trademark Rehydrol II from Reheis Corp., New Jersey.
[2] A 2,4,4'-trichloro-2'-hydroxydiphenyl ether can be purchased from Ciba Geigy Corporation under the product name Irgasan DP-300.
[3] An aprotic solvent, lactamide monoethanolamine, sold under the trademark Incromectant LMEA from Croda Inc.
[4] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE V

The following antiperspirant composition was made as described in Example I. The first mixture and the second mixture contained the following constituents.

| Constituent | % (by weight) |
|---|---|
| First Mixture: | |
| Propylene Glycol | 34.7 |
| Rehydrol II[1] | 15.0 |
| Benzyl Alcohol | 20.0 |
| Isostearyl Alcohol | 5.0 |
| Irgasan DP-300[2] | 0.3 |
| Second Mixture: | |
| Dipropylene Glycol | 12.0 |
| Lactamide MEA[3] | 5.0 |
| N-methylpyrrolidone | 5.0 |
| DBMSA[4] | 3.0 |

[1] A complex of aluminum chlorohydrate and propylene glycol purchased under the trademark Rehydrol II from Reheis Corp., New Jersey.
[2] A 2,4,4'-trichloro-2'-hydroxydiphenyl ether can be purchased from Ciba Geigy Corporation under the product name Irgasan DP-300.
[3] An aprotic solvent, lactamide monoethanolamine, sold under the trademark Incromectant LMEA from Croda Inc.
[4] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE VI

The following antiperspirant composition was made as described in Example I. The first mixture and the second mixture contained the following constituents.

| Constituent | % (by weight) |
|---|---|
| First Mixture: | |
| Propylene Glycol | 34.7 |
| Rehydrol II[1] | 15.0 |
| Benzyl Alcohol | 20.0 |
| Isostearyl Alcohol | 10.0 |
| Irgasan DP-300[2] | 0.3 |
| Second Mixture: | |
| Dipropylene Glycol | 12.0 |
| Lactamide MEA[3] | 5.0 |
| DBMSA[4] | 3.0 |

[1] A complex of aluminum chlorohydrate and propylene glycol purchased under the trademark Rehydrol II from Reheis Corp., New Jersey.
[2] A 2,4,4'-trichloro-2'-hydroxydiphenyl ether can be purchased from Ciba Geigy Corporation under the product name Irgasan DP-300.
[3] An aprotic solvent, lactamide monoethanolamine, sold under the trademark Incromectant LMEA from Croda Inc.
[4] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE VII

The following antiperspirant composition was made as described in Example I. The first mixture and the second mixture contained the following constituents.

| Constituent | % (by weight) |
|---|---|
| First Mixture: | |
| Propylene Glycol | 34.7 |
| Rehydrol II[1] | 15.0 |
| Dipropylene Glycol Methyl Ether | 10.0 |
| Isostearyl Alcohol | 12.0 |
| Irgasan DP-300[2] | 0.3 |
| Second Mixture: | |
| Dow Corning 193[3] | 15.0 |
| Lactamide MEA[4] | 5.0 |
| N-methylpyrrolidone | 5.0 |

| Constituent | % (by weight) |
| --- | --- |
| DBMSA[5] | 3.0 |

[1] A complex of aluminum chlorohydrate and propylene glycol purchased under the trademark Rehydrol II from Reheis Corp., New Jersey.
[2] A 2,4,4'-trichloro-2'-hydroxydiphenyl ether can be purchased from Ciba Geigy Corporation under the product name Irgasan DP-300.
[3] A dimelthicone copolyol from Dow Corning, Midland, Michigan.
[4] An aprotic solvent, lactamide monoethanolamine, sold under the trademark Incromectant LMEA from Croda Inc.
[5] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

EXAMPLE VIII

The following antiperspirant composition was made as described in Example I. The first mixture and the second mixture contained the following constituents.

| Constituent | % (by weight) |
| --- | --- |
| First Mixture: | |
| Propylene Glycol | 34.7 |
| Rehydrol II[1] | 15.0 |
| Dipropylene Glycol Methyl Ether | 10.0 |
| Isostearyl Alcohol | 12.0 |
| Dow Corning 193[2] | 5.0 |
| Irgasan DP-300[3] | 0.3 |
| Second Mixture: | |
| Hexylene Glycol | 15.0 |
| Lactamide MEA[4] | 5.0 |
| DBMSA[5] | 3.0 |

[1] A complex of aluminum chlorohydrate and propylene glycol purchased under the trademark Rehydrol II from Reheis Corp., New Jersey.
[2] A dimelthicone copolyol from Dow Corning, Midland, Michigan.
[3] A 2,4,4'-trichloro-2'-hydroxydiphenyl ether can be purchased from Ciba Geigy Corporation under the product name Irgasan DP-300.
[4] An aprotic solvent, lactamide monoethanolamine, sold under the trademark Incromectant LMEA from Croda Inc.
[5] Dibenzyl monosorbitol acetal (DBMSA) commercially available from New Japan Chemical Co., Ltd. under the tradename Gell-All-D and Milliken Chemical, Division of Milliken & Company and under the product name Millithix 925.

All of the antiperspirant compositions produced in Examples I–VIII had excellent efficacy with all of the desirable features described herein. For example, the antiperspirant compositions produced according to Examples I–VIII were relatively odorless, stable, and translucent. In addition, the individual constituents of each antiperspirant composition were uniformly distributed.

Having described the invention in detail and by reference to preferred embodiments thereof, it will be apparent that modifications and variations are possible without departing from the scope of the invention which is defined in the appended claims.

What is claimed is:

1. An antiperspirant stick composition comprising:
   (a) from about 15% to about 25% by weight of an acidic antiperspirant active metal salt;
   (b) from about 1% to about 70% by weight of a polar solvent which is not a monohydric alcohol;
   (c) from about 5% to about 15% by weight of an aprotic solvent;
   (d) from about 2% to about 5% by weight of a gelling agent; and
   (e) from about 0.05% to about 0.3% by weight of an antimicrobial agent.

2. The composition of claim 1 wherein said acidic antiperspirant active metal salt comprises a complex of aluminum chlorohydrate and propylene glycol.

3. The composition of claim 1 wherein said polar solvent is selected from the group consisting of propylene glycol, hexylene glycol, dipropylene glycol, dimethicone copolyol, dipropyl glycol methyl ether, ethylene glycol phenyl ether, isostearyl alcohol and benzyl alcohol.

4. The composition of claim 1 wherein said polar solvent comprises from about 20% to about 50% propylene glycol.

5. The composition of claim 1 wherein said aprotic solvent is selected from the group consisting of lactamide monoethanolamine and N-methylpyrrolidone.

6. The composition of claim 1 wherein said gelling agent comprises dibenzyl monosorbitol acetal.

7. The composition of claim 1 wherein said antimicrobial agent comprises 2,4,4'-trichloro-2'-hydroxydiphenyl ether.

8. An antiperspirant stick composition comprising:
   (a) from about 15% to about 25% by weight of a complex of aluminum chlorohydrate and propylene glycol;
   (b) from about 1% to about 70% by weight of a polar solvent which is not a monohydric alcohol, said polar solvent being selected from the group consisting of propylene glycol, hexylene glycol, dipropylene glycol, dimethicone copolyol, dipropyl glycol methyl ether, ethylene glycol phenyl ether, isostearyl alcohol and benzyl alcohol;
   (c) from about 5% to about 15% by weight of an aprotic solvent selected from the group consisting of lactamide monoethanolamine and N-methylpyrrolidone;
   (d) from about 2% to about 5% by weight of a gelling agent; and
   (e) from about 0.05% to about 0.3% by weight of an antimicrobial agent.

9. The composition of claim 8 wherein said gelling agent comprises dibenzyl monosorbitol acetal.

10. The composition of claim 8 wherein said antimicrobial agent comprises 2,4,4'-trichloro-2'-hydroxydiphenyl ether.

11. An antiperspirant stick composition comprising:
    (a) about 15% by weight of a complex of aluminum chlorohydrate and propylene glycol;
    (b) about 35% by weight propylene glycol;
    (c) from about 10% to about 20% by weight dipropylene glycol;
    (d) from about 10% to about 20% by weight dipropylene glycol methyl ether;
    (e) about 10% by weight of an aprotic solvent;
    (f) from about 5% to about 25% by weight of a branched chain alcohol;
    (g) about 3% by weight dibenzyl monosorbitol acetal; and
    (h) about 0.3% by weight 2,4,4'-trichloro-2'-hydroxydiphenyl ether.

12. The composition of claim 11 wherein said aprotic solvent is selected from the group consisting of lactamide monoethanolamine and N-methylpyrrolidone.

13. An antiperspirant stick composition comprising:
    (a) about 15% by weight of a complex of aluminum chlorohydrate and propylene glycol;
    (b) about 35% by weight propylene glycol;
    (c) from about 10% to about 20% by weight of hexylene glycol;
    (d) from about 10% to about 20% by weight of ethylene glycol phenyl ether;

(e) about 10% by weight of an aprotic solvent selected from the group consisting of lactamide monoethanolamine and N-methylpyrrolidone;

(f) from about 5% to about 25% by weight of a branched chain alcohol;

(g) about 3% by weight dibenzyl monosorbitol acetal; and (h) about 0.3% by weight 2,4,4'-trichloro-2'-hydroxydiphenyl ether.

14. The composition of claim 13 wherein said branched chain alcohol is selected from the group consisting of isostearyl alcohol and benzyl alcohol.

15. A method of making an antiperspirant stick composition comprising the steps of:

preparing a first mixture by dissolving an acidic antiperspirant active metal salt in a first polar solvent;

preparing a second mixture by dissolving a gelling agent in a second polar solvent and an aprotic solvent;

pouring said first mixture into said second mixture so as to obtain a homogenous solution; and pouring said homogenous solution into a mold having a predetermined shape and allowing said homogenous solution to gel, thereby forming said stick composition.

16. The method of claim 15 wherein said step of preparing said first mixture comprises the step of simultaneously mixing and heating said active metal salt and said first polar solvent so as to dissolve said active metal salt in said first polar solvent.

17. The method of claim 15 wherein said step of preparing said second mixture comprises the step of simultaneously mixing and heating said gelling agent in said second polar solvent and said aprotic solvent so as to dissolve said gelling agent in said second polar solvent and said aprotic solvent.

18. The method of claim 15 wherein said first polar solvent comprises propylene glycol and said active metal salt comprises a complex of aluminum chlorohydrate and propylene glycol.

19. The method of claim 15 wherein said gelling agent comprises dibenzyl monosorbitol acetal, said second polar solvent comprises dipropylene glycol and hexylene glycol, and said aprotic solvent is selected from the group consisting of lactamide monoethanolamine and N-methylpyrrolidone.

20. The method of claim 15 further including the step of adding an antimicrobial agent to said second mixture.

* * * * *